(12) United States Patent
Yasunaga

(10) Patent No.: US 6,962,563 B2
(45) Date of Patent: Nov. 8, 2005

(54) SURGICAL APPARATUS

(75) Inventor: Koji Yasunaga, Hino (JP)

(73) Assignee: Olympus Corporation (JP)

( * ) Notice: Subject to any disclaimer, the term of this patent is extended or adjusted under 35 U.S.C. 154(b) by 131 days.

(21) Appl. No.: 10/246,140

(22) Filed: Sep. 17, 2002

(65) Prior Publication Data

US 2003/0055437 A1 Mar. 20, 2003

(30) Foreign Application Priority Data

Sep. 19, 2001 (JP) .......................................... 2001-285829

(51) Int. Cl.[7] .............................................. A61B 1/04

(52) U.S. Cl. ........................ 600/114; 600/121; 600/122

(58) Field of Search ................................. 600/114, 121, 600/122, 112, 123, 124, 125, 101, 102, 109, 111, 163, 167, 171; 606/130

(56) References Cited

U.S. PATENT DOCUMENTS

| | | | | |
|---|---|---|---|---|
| 4,538,594 A | * | 9/1985 | Boebel et al. ................. | 128/6 |
| 4,620,547 A | * | 11/1986 | Boebel ........................ | 128/754 |
| 4,807,593 A | * | 2/1989 | Ito ................................ | 128/4 |
| 4,991,564 A | * | 2/1991 | Takahashi et al. ............. | 128/4 |
| 5,441,042 A | * | 8/1995 | Putman ....................... | 601/109 |
| 5,486,155 A | * | 1/1996 | Muller et al. ............... | 600/137 |
| 5,697,939 A | | 12/1997 | Kubota et al. ............. | 606/130 |
| 5,928,137 A | * | 7/1999 | Green ......................... | 600/160 |
| 6,142,931 A | | 11/2000 | Kaji ........................... | 600/114 |

* cited by examiner

Primary Examiner—Julian W. Woo
Assistant Examiner—Charles H. Sam
(74) Attorney, Agent, or Firm—Ostrolenk, Faber, Gerb & Soffen, LLP

(57) ABSTRACT

A surgical apparatus comprises a rigid sheath, an object observation mechanism and an observation optical axis rotating mechanism. The sheath has a distal opening and a proximal opening. The object observation mechanism is inserted into the sheath from the proximal opening. The observation optical axis rotating mechanism rotates the object observation mechanism about the axis of the sheath.

87 Claims, 8 Drawing Sheets

SURGICAL APPARATUS

CROSS-REFERENCE TO RELATED APPLICATIONS

This application is based upon and claims the benefit of priority from the prior Japanese Patent Application No. 2001-285829, filed Sep. 19, 2001, the entire contents of which are incorporated by reference.

BACKGROUND OF THE INVENTION

1. Field of the Invention

The present invention relates to a surgical apparatus that can be inserted into an intracavital of a patient to thereby treat an affected area while observing the area using, for example, an endoscope.

2. Description of the Related Art

In recent surgical operations, a working space is secured by inserting a cylindrical sheath into an intracavital of a patient. The to-be-treated portion is observed by an endoscope inserted in the sheath. The to-be-treated portion or affected portion is treated by a surgical instrument inserted in a space between the endoscope and sheath. This technique is now widely used to reduce the invasiveness.

In the field of cerebral nerve surgery, endoscopic surgical operations using such a sheath have been recently demanded.

U.S. Pat. No. 6,142,931 has proposed, an example of an endoscopic surgical apparatus using a sheath. In this apparatus, an endoscope having an oblique-viewing angle of 30° or more with respect to the axis of its insertion section is provided in a sheath. The insertion section of the endoscope is arranged on the circumference of the sheath around the axis.

U.S. Pat. No. 5,697,939 discloses a holder apparatus. This apparatus fixes one point of the endoscope insertion section so that the insertion section can only rotate about the one point. This enables the field of view to be changed within an intracavital of a patient.

BRIEF SUMMARY OF THE INVENTION

According to an aspect of the invention, there is provided a surgical apparatus comprising:

a rigid sheath having a distal end having a distal opening, a circular proximal end having a proximal opening, and an axis;

an object observation mechanism having an observation optical axis inclined to the axis of the sheath, the object observation mechanism being inserted into the sheath; and an observation optical axis rotating mechanism for rotating the object observation mechanism about the axis of the sheath.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Preferred embodiments of the invention will be described with reference to the accompanying drawings.

Figure 1:
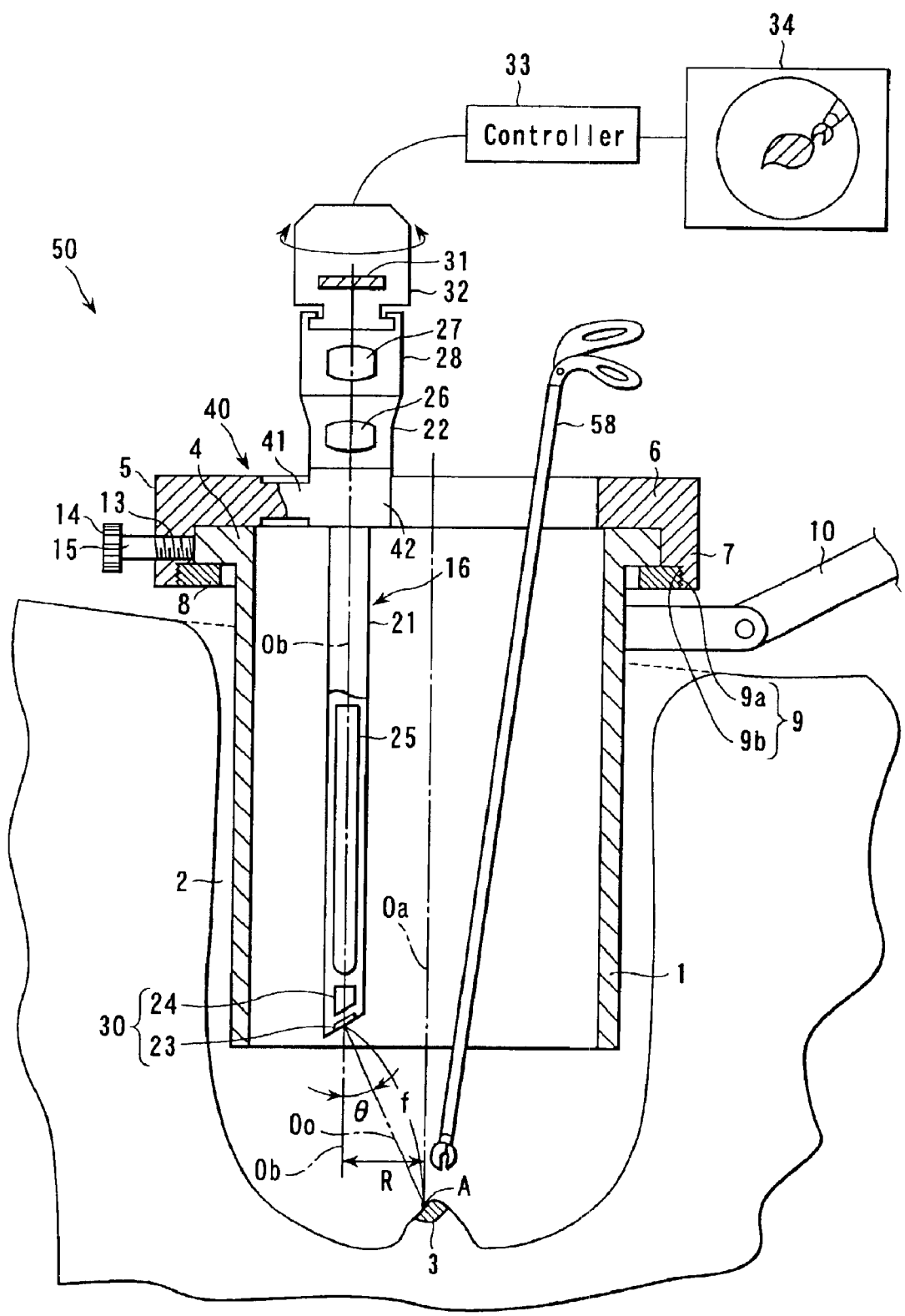
FIG. 1 is a schematic side view, illustrating the entire structure of an endoscopic surgical apparatus according to a first embodiment of the invention.
Figure 2A:
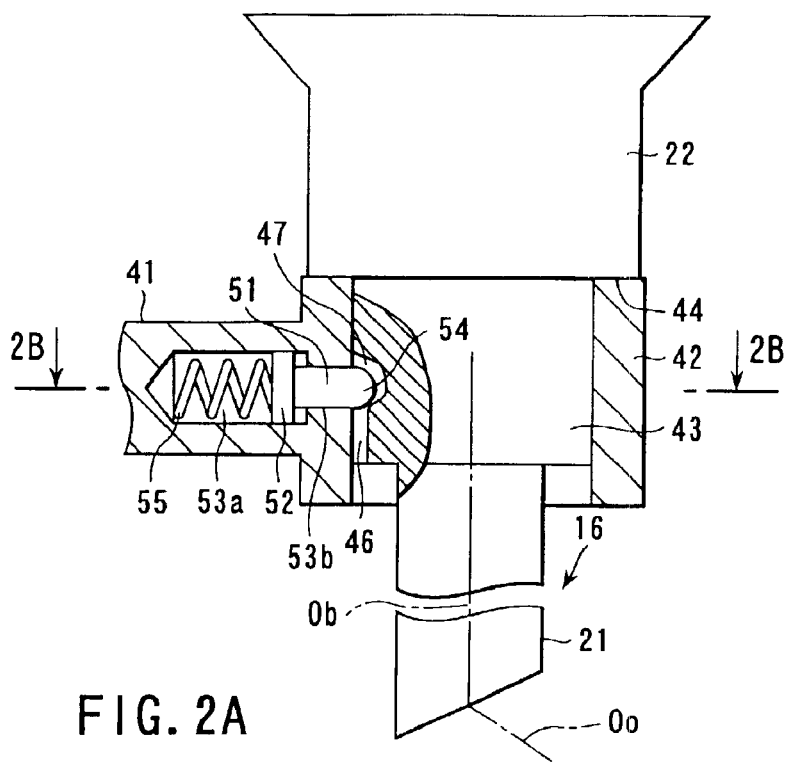
FIG. 2A is a side view illustrating the endoscope shown in FIG. 1 that includes an insertion axis Ob with respect to the holding cylinder shown in FIG. 1.
Figure 2B:
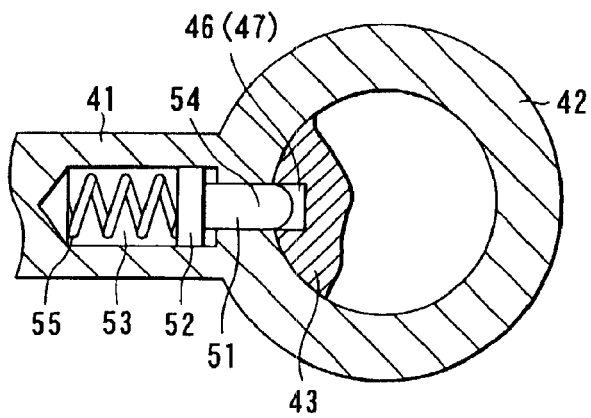
FIG. 2B is a view taken along line 2B—2B of FIG. 2A.
Figure 3:
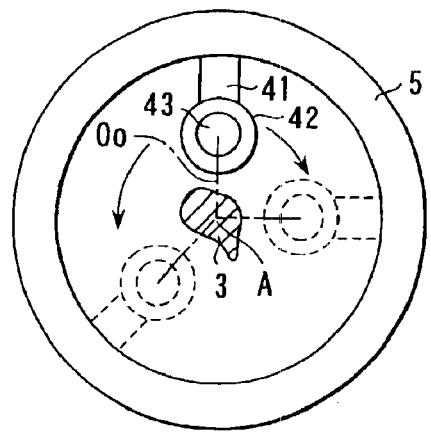
FIG. 3 is a plan view illustrating a sheath, as viewed from above, employed in the endoscopic surgical apparatus of the first embodiment.

Referring first to FIGS. 1 to 3, a first embodiment of the invention will be described. FIG. 1 is a schematic view partly in section, illustrating the entire structure of an endoscopic surgical system 50 according to the first embodiment.

An endoscope 16 employed in the system 50 is a rigid-type endoscope. As seen from FIG. 1, the endoscope 16 comprises an elongated insertion section 21 and eyepiece section (hand-side section) 22 located at the hand-side end of the insertion section 21. It is preferable that the insertion section 21 and eyepiece portion 22 have respective circular cross sections. The insertion section 21 has an insertion axis Ob. It is preferable that the insertion section 21 and eyepiece portion 22 are coaxial. In other words, the insertion section 21 and eyepiece portion 22 preferably have the same axis Ob.

An object optical system 30 including an objective lens 23 and prism 24 is provided at the distal end of the insertion section 21 of the endoscope 16. The observation optical axis Oo of the object optical system 30 is inclined at an angle θ with respect to the insertion axis Ob of the insertion section 21. The observation optical axis Oo of the object optical system 30 is separate from the insertion axis Ob near the lower end of the prism 24 (i.e., at the objective lens 23). On the contrary, from the patient 3 side, the observation optical axis Oo of the object optical system 30 coincides with the insertion axis Ob near the prism 24.

A relay lens 25 for relaying the image entering the object optical system 30 is provided in the insertion section 21. The eyepiece portion 22 has an eyepiece 26 for receiving the image transmitted through the relay lens 25.

An interchangeable tip 28 having an imaging lens 27 is provided integrally with the upper end (proximal end) of the eyepiece portion 22. A TV camera 32 containing a CCD 31 as an image pickup element is rotatably connected to the upper end of the interchangeable tip 28, and arranged coaxially with the endoscope 16.

Thus, the object optical system 30, relay lens 25, eyepiece 26, imaging lens 27 and CCD 31 are arranged on the insertion axis Ob. The TV camera 32 is connected to a TV monitor 34 via a controller 33 having a video signal processing function.

The endoscope 16 also comprises an illumination optical system (not shown) for illuminating an affected area 3, and a light guide (not shown) for guiding the light emitted from a light source (not shown), to the illumination optical system. An illumination light transmissions mechanism for guiding the light from the light source is connected to the light guide. Thus, light is guided from the light source to the illumination optical system via the illumination light transmission mechanism and light guide.

AS shown in FIGS. 2A and 2B, a connection portion 43 having a smaller diameter than the eyepiece portion 22 is formed in the vicinity of an end of the eyepiece section 22. The outer diameter of the connection portion 43 is between the outer diameters of the insertion section 21 and eyepiece portion 22 of the endoscope 16. It is preferable that the end surfaces (boundary portions; stepped portions) 44 of the insertion section 21 and eyepiece portion 22 with respect to the connection portion 43 are perpendicular to the insertion axis.

As shown in FIG. 1, the endoscopic surgical system 50 has a sheath 1 formed of a rigid hollow cylindrical member having a distal opening and proximal opening. The sheath 1 has an axis Oa that passes through the respective central points of the distal and proximal openings. The sheath 1 is inserted into an opening 2 formed in, for example, the head of a patient (object). The observation or treatment of the affected area 3 located at the bottom of the opening 2 in the head of the patient is executed through the sheath 1. The sheath 1 is fixed to, for example, an operating table (not shown), by means of a holder arm 10.

An outwardly projecting annular flange 4 is formed at the proximal opening (hand-side opening) of the sheath 1. The axis of the flange 4 is identical to that of the sheath 1, Oa. A cylindrical rotary ring (rotary cylinder) 5 is detachably attached to the flange 4.

The rotary ring 5 has a ring portion 6 in contact with the upper end (hand-side end) of the flange 4, and a cover portion 7 that project from the outer periphery of the ring portion 6 along the axis of the sheath 1 and covers the outer periphery of the flange 4. A screw portion 9a is formed at the inner peripheral surface of the edge of the cover portion 7.

A fitting ring 8 is fitted on the side of the ring 5 opposing the ring portion 6 with the flange 4 interposed therebetween. A screw portion 9b engaged with the aforementioned screw portion 9a is formed at the outer periphery of the fitting ring 8. When the screw portions 9a and 9b are engaged with each other, drop of the rotary ring 5 is prevented. As a result, the rotary ring 5 is kept in contact with the flange 4.

In this state, the rotary ring 5 is in contact with the hand-side end of the flange 4 and is rotatable about the axis Oa of the sheath 1. The hand-side end surface of the flange 4 is in contact with the inner surface of the ring portion 6 opposite its hand-side end surface such that the contact surfaces can smoothly slide relative to each other. Further, the surface of the flange 4 opposite its hand-side surface is in contact with the inner surface of the ring 8 such that the contact surfaces can smoothly slide relative to each other.

The cover portion 7 of the rotary ring 5 has a screw hole 13 formed therethrough from the outer periphery to the inner periphery, i.e., toward the axis Oa. A fastening screw 15 having a tab 14 is screwed into the screw hole 13. When the tip of the fastening screw 15 is pressed against the outer periphery of the flange 4, the rotation of the rotary ring 5 around the flange 4 is stopped. On the other hand, when the tip of the fastening screw 15 is separated from the outer periphery of the flange 4, the rotary ring 5 can rotate around the flange 4. Thus, an engagement mechanism for engaging and disengaging the rotary ring 5 with and from the flange 4 is realized.

A description will now be given of a rotary support mechanism 40 for supporting the endoscope 16 such that the endoscope can rotate about the axis Oa of the sheath 1. As shown in FIGS. 1 and 3, the rotary support mechanism 40 comprises the aforementioned rotary ring 5, a holding arm 41 projecting from the rotary ring 5 and formed integrally as one body with the inner periphery of the ring 5, and a holding cylinder 42 formed at the distal end of the holding arm 41. The upper surface of the holding cylinder 42 is parallel to the hand-side end surface of the sheath 1. Further, the axis of the holding cylinder 42 is displaced by a distance (radius) R from the axis Oa of the sheath 1. It is preferable that the position of the holding cylinder 42 along the axis of the sheath 1 can be varied in accordance with the focal point of the endoscope 16. This can be realized by, for example, preparing a plurality of rotary support mechanisms 40 and exchanging one for another.

As shown in FIGS. 2A and 2B, the aforementioned connection portion 43 of the endoscope 16 is fitted in the holding cylinder 42 of the rotary support mechanism 40. Accordingly, the endoscope 16 is held so that it can rotate about the insertion axis Ob. When the connection portion 43 is fitted in the holding cylinder 42, the upper surface of the connection portion 43 is level with the upper end of the holding cylinder 42.

As shown in FIGS. 2A and 2B, a slit 46 having a predetermined width is formed in the outer periphery of the connection portion 43 along the insertion axis Ob. For example, the slit 46 is positioned opposite the observation optical axis Oo with respect to the insertion axis Ob of the endoscope 16 (i.e., displaced by 180° from the axis Oo). Furthermore, an engagement recess 47 is formed in the slit 46, deeper than the other portions of the connection portion 43.

A hole 53a is formed in the holding arm 41 near the boundary of the holding arm 41 and holding cylinder 42. A hole 53b extends from the hole 53a through the wall of the holding cylinder 42. The base portion 52 of a fixing pin 51 having a T-shaped cross section is inserted in the hole 53a. Further, a press spring 55 that presses the base portion 52 into the holding cylinder 42 is contained in the hole 53a. The tip 54 of the fixing pin 51 is pressed by the spring 55 toward the insertion axis Ob of the endoscope 16 (into the holding cylinder 42). In other words, the tip 54 of the fixing pin 51 is always pressed such that it projects into the holding cylinder 42. Thus, the tip 54 of the fixing pin 51 is arranged so that it can project and retract into and from the holding cylinder 42 through the wall of the cylinder. The tip 54 of the fixing pin 51 is fitted in the slit 46 of the endoscope 16 held in the holding cylinder 42, and is received in the engagement recess 47. As a result, the endoscope 16 is fixed in position with respect to the axis of the holding cylinder 42, and at the same time, is fixed in the circumferential direction of the holding cylinder 42.

The width of the slit 46 is determined based on the diameter of the tip 54 of the fixing pin 51, so that the tip 54 can be fitted in the slit 46.

As described above, in the embodiment, a positioning mechanism for positioning the endoscope 16 at a predetermined position is realized by the holding cylinder 42, fixing pin 51, press spring 55, slit 46 of the endoscope 16 and engagement recess 47.

Referring again to FIG. 1, the optical positional relationship concerning the observation using the endoscope 16 will be described. As seen from FIG. 1, the insertion axis Ob of the endoscope 16 is parallel to the axis Oa of the sheath 1, and is displaced therefrom by the distance R. Accordingly, the observation optical axis Oo is pivoted about the axis Oa of the sheath 1, always directed to the axis Oa.

Further, the angle θ formed between the focal distance f of the endoscope 16 and the observation optical axis Oo is given by R=f sin θ (R is the aforementioned distance)

Point A, the focal point of the endoscope 16 on the observation optical axis Oo, is always positioned on the axis Oa of the sheath 1. The point A is the center of the field of view, and is the axis about which the endoscope 16 is rotated by the rotary support mechanism 40.

The operation of the endoscopic surgical system of the embodiment will be described. Firstly, the preparation executed before the sheath 1 and endoscope 16 are inserted into the body of a patient will be described.

As shown in FIG. 1, the sheath 1 and rotary ring 5 are made unrotatable relative to each other by the fastening screw 15. The endoscope 16 is inserted into the holding cylinder 42 with the sheath 1 attached thereto. At this time, as shown in FIGS. 2A and 2B, the insertion is executed with the slit 46 of the connection portion 43 of the endoscope 16 aligned with the fixing pin 51. The fixing pin 51 is fitted into the recess 47 of the slit 46. At this time, the axial position of the holding cylinder 42 is adjusted so that the intersection of the axis Oa of the sheath 1 and the observation optical axis Oo is positioned at the point A. Further, the tip 54 of the fixing pin 51 is engaged with the engagement recess 47, thereby fitting the endoscope 16 in the holding cylinder 42 firmly in both the axial and circumferential directions.

Thus, the endoscope 16 is held in the sheath 1, thereby forming the endoscopic surgical system 50. Then, the endoscopic surgical system 50 is inserted into the opening 2 formed in the body, e.g. the head, of the patient, as shown in FIG. 1. At this time, the affected area 3 is positioned at the point A, i.e., the focus at which the axis Oa of the sheath 1 and the observation optical axis Oo intersect each other. In this state, the sheath 1 is fixed to, for example, an operating table by the holder arm 10.

A description will now be given of how the affected area 3 is observed. An image of the affected area 3 is transmitted to the eyepiece portion 22 via the objective lens 23, prism 24, relay lens 25 and eyepiece 27 of the endoscope 16. The image is further transmitted to the CCD 31 of the TV camera 32 via the imaging lens 27 of the interchangeable tip 28. It is further transmitted from the CCD 31 to the TV monitor 34 via the controller 33, whereby the image of the affected area 3 is displayed thereon.

To treat the affected area 3, a surgical instrument 58 such as forceps is inserted into the space of the sheath 1 as shown in FIG. 1. When starting the treatment, to facilitate the operation of the surgical instrument 58, a surgeon rotates the TV camera 32 (CCD 31) about the insertion axis Ob relative to the interchangeable tip 28. At this time, the orientation of the observation image displayed on the TV monitor 34 is adjusted to be identical to that of the affected area to be actually operated.

A description will be then given of how the direction of observation is changed with the affected area 3 fixed at the center of the field of view. Firstly, the tab 14 is rotated to loosen the fastening screw 15. After that, the rotary ring 5 is rotated about the axis Oa of the sheath 1. At this time, the endoscope 16 is rotated about the axis Oa of the sheath 1 together with the holding cylinder 42 and arm 41. The endoscope 16 is positioned so that the axis Oa is always separate from the insertion axis Ob by the distance R. In other words, the endoscope 16 is moved along the circle of the radius R using the axis Oa as its central point. The observation optical axis Oo draws a conical locus using the point A (affected area 3) as the apex. Thus, the observation direction of the endoscope 16 is changed while the observation optical axis Oo is pivoted on the point A.

FIG. 3 is a view assumed when the axis Oa in FIG. 1 is viewed from above, showing various positions of the endoscope 16. For example, there is a case where the surgeon wants to see the back of the affected area 3 as a front view, when the endoscope 16 is positioned as indicated by the solid line in FIG. 3. At this time, the endoscope 16 is rotated through 180° about the axis Oa as indicated by the broken line in FIG. 3. The point A of the observation field is positioned at the focal distance f of the endoscope 16, and hence the affected area 3 is kept in focus. Therefore, the direction in which the affected area 3 is seen can be selected optionally.

If the TV camera 32 is rotated in accordance with the rotation of the endoscope 16, the orientation of the observation image on the TV monitor 34 will differ from that of the affected area 3 which the surgeon actually observes. In light of this, the TV camera 32 is rotated relative to the interchangeable tip 28 to adjust the orientation of the observation image.

In the embodiment, the rotary support mechanism 40 is rotated with the rotary ring 5 engaged with the flange 4 of the sheath 1. Further, the linear bar-like holding arm 41 holds the endoscope 16. This means that the direction of the observation optical axis Oo of the endoscope 16 is limited by the mechanical position fixing. In other words, the support mechanism 40 enables the inner space of the sheath 1 to be used effectively, i.e., secures a wide operation space for the surgical instrument 58.

This embodiment is applicable to a rigid-type endoscope having a particular shape that enables observation in a direction oblique to the insertion axis Ob. Further, since the embodiment does not require an optical deviating mechanism, it can exhibit optical performance identical to that of the conventional endoscopic observation.

In the embodiment, the position of the endoscope 16 is fixed by the fixing pin 51 for fixing the endoscope to the holding cylinder 42. Alternatively, a light-guide connecting portion (not shown) incorporated in the endoscope 16, for example, may be used as a positioning mechanism.

Figure 4:
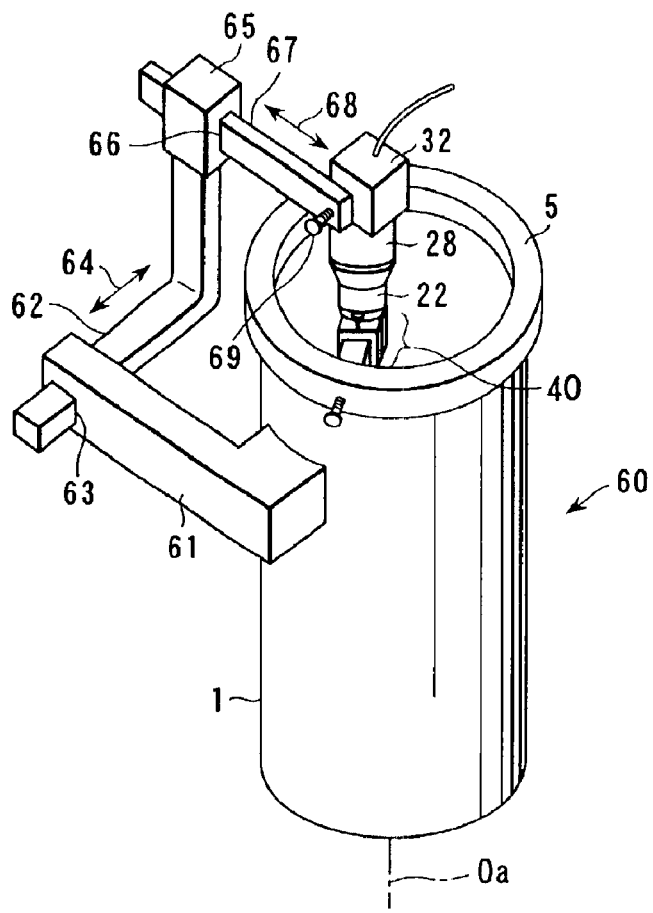
FIG. 4 is a perspective view illustrating an endoscopic surgical apparatus according to a second embodiment of the invention.
Figure 5:
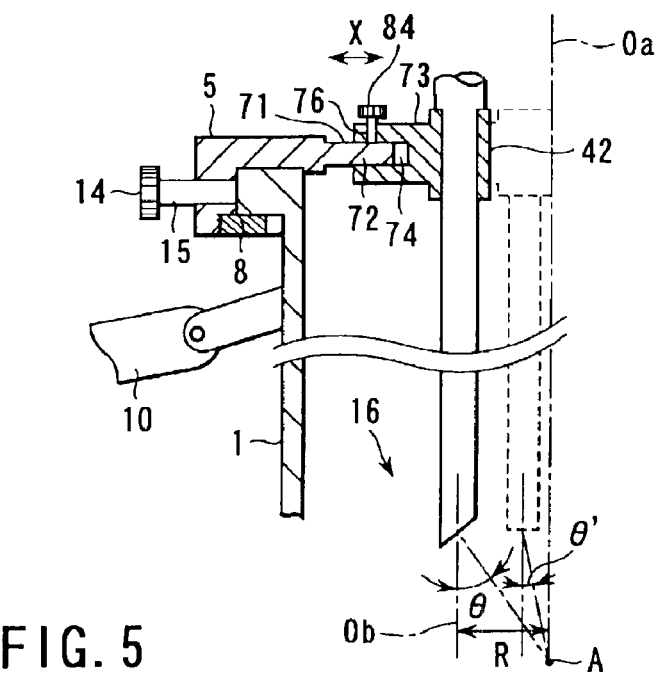
FIG. 5 is a sectional view illustrating a rotary support mechanism employed in the surgical apparatus shown in FIG. 4.

Referring to FIGS. 4 and 5, a second embodiment will be described. This embodiment is a modification of the first embodiment. In the second embodiment, elements similar to those of the first embodiment are denoted by corresponding reference numerals, and no detailed description is given thereof.

As shown in FIG. 4, in an endoscopic surgical apparatus 60 according to the second embodiment, a first support arm 61 is formed integrally as one body with the outer periphery of the sheath 1. The first support arm 61 extends perpendicular to the axis Oa of the sheath 1. A through hole 63 having a rectangular cross section is formed in the distal end of the first support arm 61. A second support arm 62 having a rectangular cross section is inserted through hole 63. The end of the second support arm 62 close to the through hole 63 is perpendicular to the first support arm 61. The second support arm 62 is movable in the directions indicated by arrows 64.

The second support arm 62 is bent into an L shape. The other end of the second support arm 62 remote from the through hole 63 is located parallel to the axis Oa of the sheath 1. A block 65 is formed integrally as one body with the other end of the second support arm 62. A through hole 66 having a rectangular cross section, similar to the through hole 63 of the first support arm 61, is formed in the block 65. The through hole 66 extends perpendicular to the through hole 63 and the other end of the second support arm 62. A third support arm 67 having a rectangular cross section is inserted in the through hole 66. The third support arm 67 is movable along the axis of the through hole 66, i.e., in the directions, indicated by arrows 68, perpendicular to the second support arm 62. A TV camera 32 is detachably attached to the other end of the third support arm 67 by a fixing screw 69. The arrows 64 are perpendicular to the arrows 68, and both the arrows 64 and 68 are perpendicular to the axis Oa of the sheath 1.

Referring to FIG. 5, the rotary support mechanism 40 for supporting the endoscope 16 will be described. A first holding arm 71 is formed integrally as one body with the inner surface of the rotary ring 5, projecting therefrom. The projecting end of the first holding arm 71 serves as a guide portion 72 having a rectangular cross section. A second holding arm 73 is formed integrally as one body with the holding cylinder 42, projecting therefrom. A guide hole 74 having a rectangular cross section is formed in the second holding arm 73. The guide portion 72 is inserted in the guide hole 74. As a result, the second holding arm 73 is supported so that it can move relative to the guide portion 72 in the directions indicated by arrows X. The directions of the arrows X are perpendicular to the axis Oa of the sheath 1.

A screw hole 76 reaching the guide hole 74 is formed in the second holding arm 73 in the direction parallel to the axis Oa. A fixing screw 84 having a tab is screwed in the screw hole 76. When the fixing screw 84 is screwed in the second holding arm 73, the tip of the screw 84 is pressed against the sidewall of the guide portion 72 inserted in the guide hole 74. The second holding arm 73 can be fixed to a desired portion of the first holding arm 71 by fastening the guide portion 72.

The endoscope 16 employed in this embodiment is useful when the angle formed between the observation optical axis Oo and insertion axis Ob is varied from θ to, for example, θ', as is indicated by the broken line in FIG. 5.

The operation of the endoscopic surgical apparatus 60 according to the embodiment will be described.

In FIG. 5, when the fixing screw 84 is loosened, the second holding arm 73 is movable relative to the first holding arm 71 in a direction perpendicular to the axis Oa. Therefore, the second holding arm 73 is moved relative to the first holding arm 71. The distance R between the insertion axis Ob of the endoscope 16 and the axis Oa of the sheath 1 is varied with the axes kept parallel. As a result, the endoscope 16 is moved as indicated by the broken line in FIG. 5, thereby selecting the angle θ' of the observation optical axis Oo relative to the insertion axis Ob. This means that even if the endoscope 16 whose angle θ between the observation optical axis Oo and the axis Ob differs from that employed in the first embodiment is used, it can provide the same advantage as the first embodiment.

Further, as shown in FIG. 4, the endoscope 16 and rotary support mechanism 40 are rotated about the axis Oa of the sheath 1. In this case, the rotation of the TV camera 32 is limited by the movement of the second support arm 62 relative to the first support arm 61, and the movement of the third support arm 67 relative to the second support arm 62. Instead, the interchangeable tip 28 rotates relative to the TV camera 32. Accordingly, the position of the TV camera 32 is maintained even when the endoscope 16 is rotated about the axis Oa. This means that the observation image on the TV monitor 34 does not rotate.

In the second embodiment, even if endoscopes whose angles θ between the observation optical axis Oo and the axis Ob differ from each other are used, the direction of observation can be varied, with the center of the field of view fixed. Accordingly, various types of endoscopes can be used. Further, to change the direction of the observation optical axis Oo relative to the axis Oa of the sheath 1, it is sufficient if the endoscope 16 is exchanged for a more appropriate one.

Further, as in the first embodiment, it is not necessary to adjust the position of the TV camera 32 when the endoscope 16 is rotated, thereby facilitating the operation.

Figure 6:
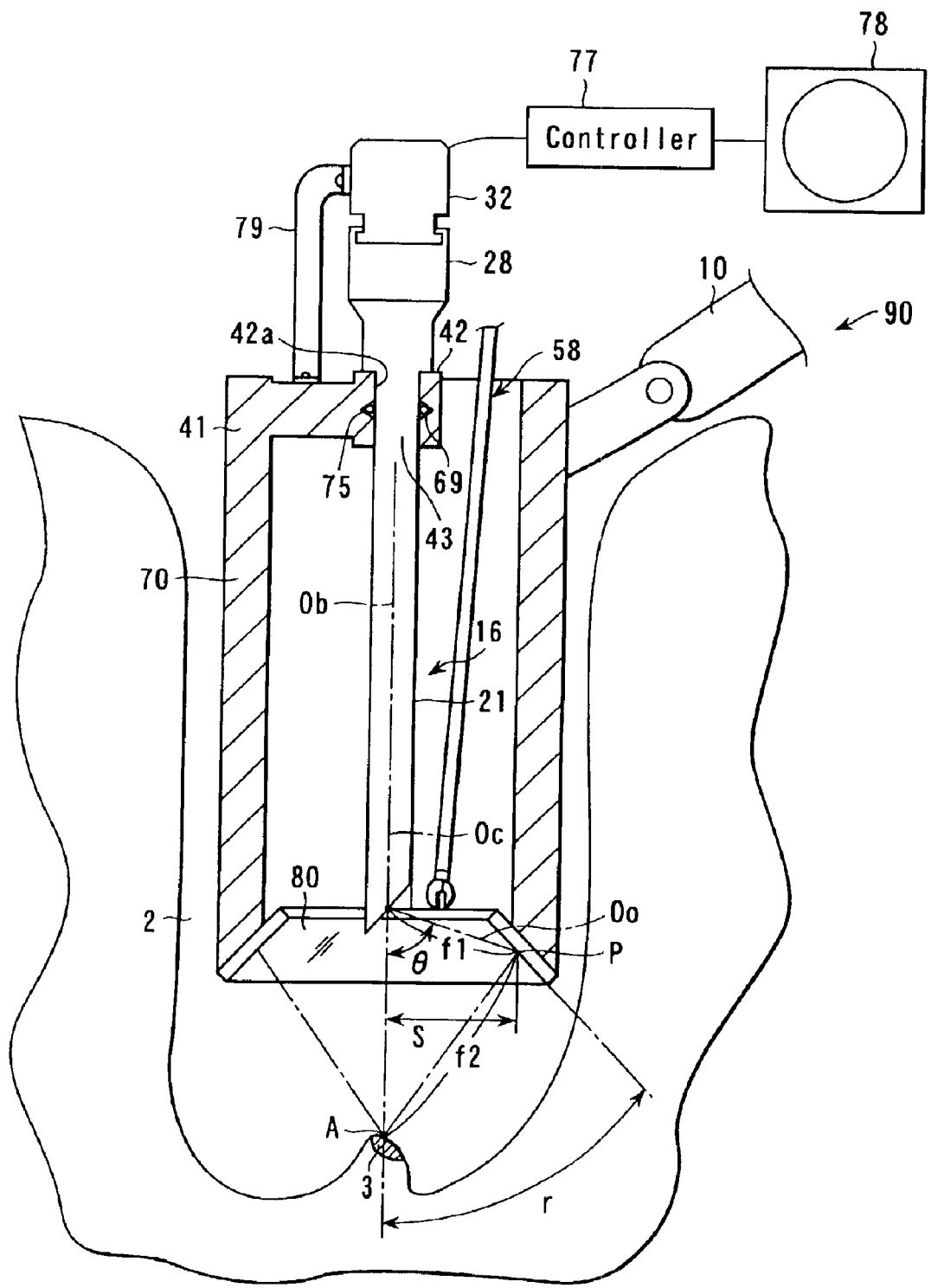
FIG. 6 is a schematic side view illustrating the entire structure of an endoscopic surgical apparatus according to a third embodiment of the invention.

Referring to FIG. 6, a third embodiment will be described. This embodiment is another modification of the first embodiment. In the third embodiment, elements similar to those of the first embodiment are denoted by corresponding reference numerals, and no detailed description is given thereof.

An endoscopic surgical system 90 according to the third embodiment employs a cylindrical sheath 70 to be inserted into an opening 2 formed in the body of a patient to observe and treat an affected area 3. The sheath 70 has an axis Oc. A holding arm 41 projecting perpendicular to the axis Oc is formed integrally as one body with the inner periphery of a proximal opening (hand-side opening). A holding cylinder 42 provided with a hole 42a having the axis Oc is formed integrally as one body with the distal end of the holding arm 41.

An annular groove 75 having a V-shaped cross section is formed in the inner periphery of the hole 42a of the holding cylinder 42. An O-ring 69 is fitted in the groove 75 in a compressed manner, interposed between the outer peripheral surface of the connecting portion 43 of the endoscope 16 and the inner peripheral surface of the holding cylinder 42. In this structure, the endoscope 16 is fixed in position but can rotate about the axis Oc. Thus, the rotary support mechanism 40 employed in this embodiment comprises the holding arm 41 and holding cylinder 42. Further, an end of a connecting arm 79 as a connector is fixed to the intermediate portion of the holding arm 41. The other end of the connecting arm 79 is fixed to the TV camera 32.

The interchangeable tip 28 and TV camera 32 are connected to the upper end of the endoscope 16 as in the first embodiment. The interchangeable tip 28 and TV camera 32 are rotatable to each other as in the first embodiment.

As seen from FIG. 6, the TV camera 32 is connected to a control unit 77 that includes a video signal processing circuit and image reversing circuit. The control unit 77 is connected to a TV monitor 78.

The distal end of the sheath 70 positioned close to the affected area 3 is in the form of a circular truncated cone. A reflection mirror 80 in the form of a circular truncated cone, which serves as an optical reflection mechanism and has the axis Oc, is attached to the entire distal end of the sheath 70. The reflection mirror 80 is tapered toward the proximal opening side of the sheath 70 at an angle γ with respect to the axis Oc.

The endoscope 16 and sheath 70 has the following optical positional relationship. Assume that the intersection of the observation optical axis Oo and the reflection surface of the reflection mirror 80 is P. In FIG. 6, f1 indicates the distance between the object 23 of the endoscope 16 and a point P on the reflection surface of the reflection mirror 80. Further, f2 indicates the distance between the point P on the reflection surface of the reflection mirror 80 and the point A. In this case, the relationship "f1+f2=f (f indicates the focal distance of the endoscope 16 as in the first embodiment)" is established. The point A as the focal point of the endoscope 16 on the observation optical axis Oo is always on the axis Oc of the sheath 70. Thus, the distance S between the axis Oc and point P, and the angle γ of the reflection mirror 80 with respect to the axis Oc are set.

Also in this embodiment, the sheath 70 is fixed to, for example, an operating table by an arm similar to the holder arm 10 of the first embodiment.

The operation of the endoscopic surgical system 90 will be described. Firstly, the preparation executed before the endoscope 16 and sheath 70 are inserted into the opening 2 of the body of a patient will be described.

The insertion section 21 of the endoscope 16 is inserted from above into the hole 42a of the holding cylinder 42 of the sheath 70. At this time, the connection portion 43 of the endoscope 16 is pressed by the O-ring 69. Accordingly, the endoscope 16 is firmly connected to the holding cylinder 42 and can rotate about the axis Oc. The endoscope 16 and sheath 70 kept in this state are inserted into the body of a patient. The sheath 70 is positioned so that the endoscopic surgical system 90 and affected area 3 have a predetermined positional relationship. At this time, the sheath 70 is secured to, for example, an operating table by the holder arm 10.

A description will now be given of how the affected area 3 is observed. An image of the affected area 3 is reflected by the conical reflection mirror 80. After that, the image is transmitted, as in the first embodiment, to the interchangeable tip 28 via the objective lens, prism, relay lens and eyepiece of the endoscope 16. The image is further transmitted from the imaging lens of the interchangeable tip 28 to the CCD of the TV camera 32. As a result, the image of the affected area 3 is displayed on the TV monitor 78 via the control unit 77. By virtue of the image reversing circuit of the control unit 77, the image displayed on the TV monitor 78 is reversed. Thus, the image is prevented from being displayed in a mirror image state.

To start an actual operation, the entire sheath 70 is rotated to rotate the TV camera 32, so that the orientation of the observation image displayed on the TV monitor 78 is identical to that of the affected area 3 the surgeon actually observes.

A description will now be given of how the direction of observation is changed with the affected area 3 fixed at the center of the field of view. The endoscope 16 is rotated about the axis Oc relative to the holding cylinder 42. At this time, the observation optical axis Oo draws a conical locus at an angle θ to the axis Oc. Further, by the conical reflection mirror 80, the observation optical axis Oo draws a conical locus using the point A as the apex. Thus, the observation direction of the endoscope 16 can be changed with the center of the field of view fixed at the point A. For example, if the surgeon wants to see the back of the affected area 3, it is sufficient if the endoscope 16 is rotated through 180° about the axis Oc.

At this time, the rotation of the TV camera 32 is prevented by the connecting arm 79. Accordingly, relative rotation occurs between the interchangeable tip 28 and TV camera 32, and hence the orientation of the observation image on the TV monitor 78 is maintained unchanged.

In this embodiment, to change the direction of observation with the center of the field of view fixed, it is sufficient if the endoscope 16 is rotated about the insertion axis Ob. Thus, the operation of the system is very simple. Further, since the endoscope 16 does not move about within the sheath 70, the endoscope 16 does not easily interrupt the operation of, for example, the surgical instrument 58.

This embodiment may be modified such that the holding arm 41, hole 42a and holding cylinder 42 are not used, and the TV camera 32 is connected to the sheath 70 by the connecting arm 79. In other words, the endoscope 16 is suspended using the connecting arm 79. In this modification, the interchangeable tip 28 connected to the TV camera 32 and the endoscope 16 are made rotatable relative to the TV camera 32.

Figure 7A:
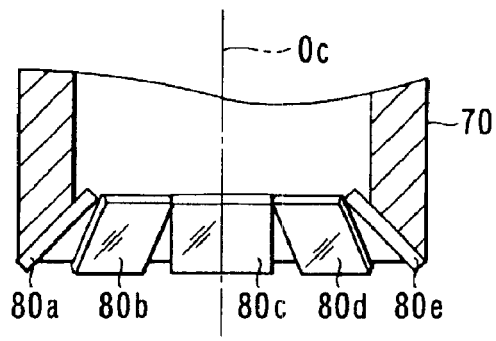
FIG. 7A is a side view illustrating the lower portion of a sheath employed in an endoscopic surgical apparatus according to a fourth embodiment.
Figure 7B:
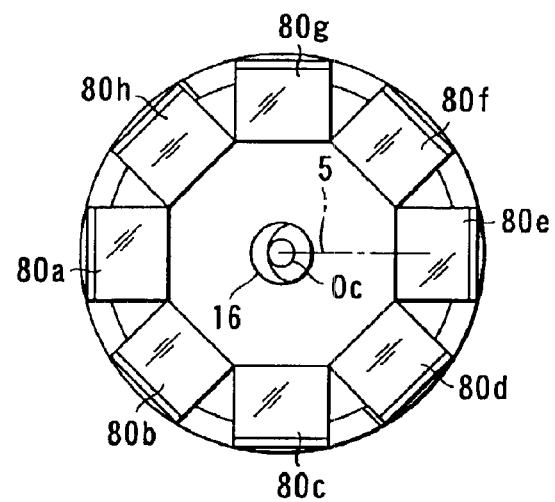
FIG. 7B is a schematic view illustrating the lower portion of the sheath of the endoscopic surgical apparatus of the fourth embodiment, as viewed from the affected area side.
Figure 8:
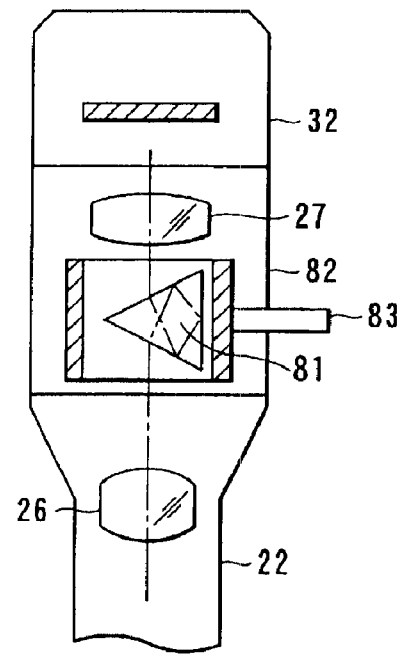
FIG. 8 is a schematic view useful in explaining the structure of an optical adaptor for the endoscopic surgical apparatus of the fourth embodiment.

Referring now to FIGS. 7A, 7B and 8, a fourth embodiment will be described. The fourth embodiment is a modification of the third embodiment. In this embodiment, elements similar to those of the third embodiment are denoted by corresponding reference numerals, and no detailed description is given thereof.

FIG. 7A is a side view illustrating the distal end of the sheath 70, and FIG. 7B is a schematic view of the distal end of the sheath 70, viewed from the affected area 3 side.

In the third embodiment, the reflection mirror 80 as an optical reflection mechanism is provided at the distal end of the sheath 70 positioned close to the affected area 3. On the other hand, in the fourth embodiment, a plurality of flat mirrors 80a–80h are employed instead of the reflection mirror 80. The flat mirrors 80a–80h provide the same function as that of the conical reflection mirror 80.

Specifically, a plurality (e.g. 8) of flat mirrors 80a–80h are inclined at the angle γ to the axis Oc as in the third embodiment, and are arranged in a circle.

In the third embodiment, an image is obtained by rotating the endoscope 16 continuously. In the fourth embodiment, the endoscope 16 is rotated step by step so that the observation optical axis Oo is aligned with one of the flat mirrors 80a–80h, thereby selecting the position of the endoscope 16. This can also change the direction of observation with the affected area 3 fixed at the center of the field of view, as in the third embodiment.

The use of the flat mirrors 80a–80h as optical reflection members in this embodiment prevents a resultant optical image from being deformed, thereby facilitating the observation.

Further, an optical adaptor 82 that contains an erecting prism 81 as shown in FIG. 8 may be used as an image reversing mechanism. In this case, a mirror image resulting from one reflection by the endoscope 16 is reversed. Specifically, an erect image results from three internal reflections, inside the erecting prism 81, of the image received from the endoscope 16. This prism 81 makes it unnecessary to employ the image reversing circuit in the control unit 77 of the third embodiment. Accordingly, the same control unit as the control unit 33 of the first embodiment can be used in the fourth embodiment.

If the optical adaptor 82 is used in the first embodiment, to adjust the orientation of the observation image, it is sufficient if the erecting prism 81 is rotated by operating the tab 83 of the optical adaptor 82. Thus, the orientation of the observation image can be adjusted by a simple operation. The erecting prism 81 can be more finely rotated by an electromotive operation.

Figure 9:
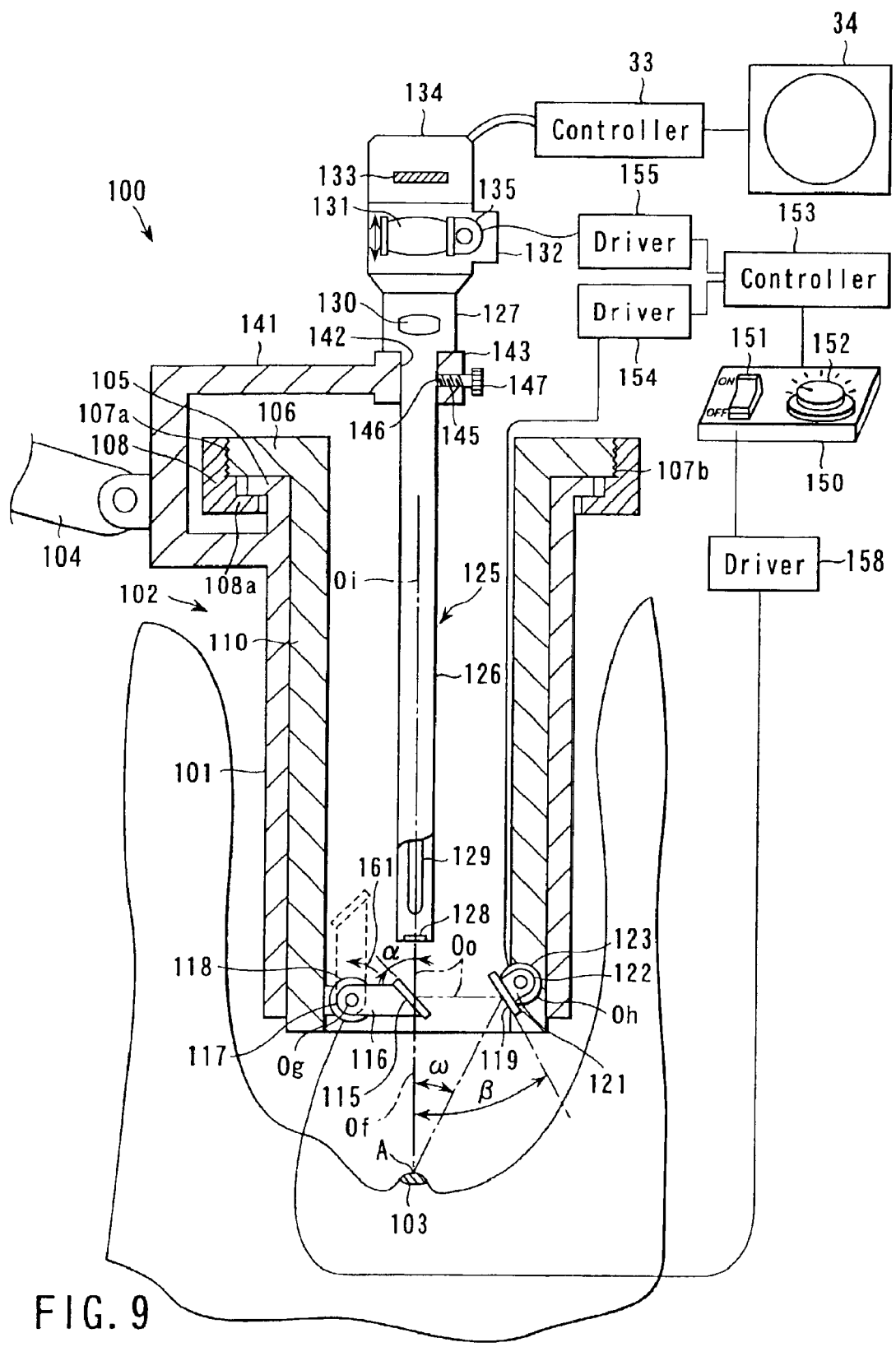
FIG. 9 is a schematic side view illustrating the entire structure of an endoscopic surgical apparatus according to a fifth embodiment of the invention.
Figure 10:
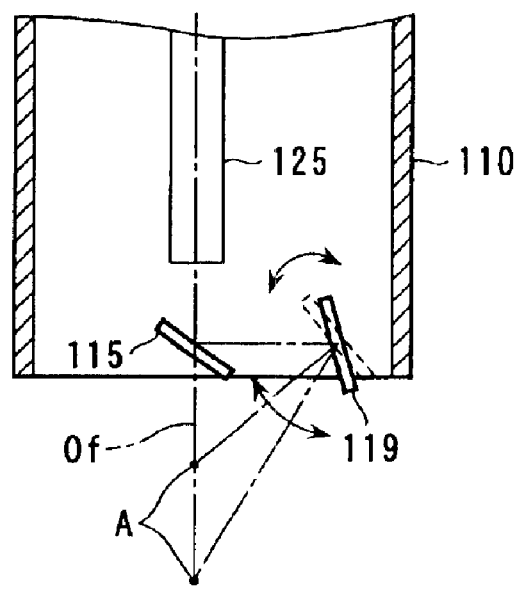
FIG. 10 is a schematic view useful in explaining the operation of the endoscopic surgical apparatus of FIG. 9.

Referring to FIGS. 9 and 10, a fifth embodiment will be described. FIG. 9 is a schematic view partly in section, illustrating the entire structure of an endoscopic surgical system 100 according to the fifth embodiment.

Firstly, an endoscope 125 for use in the endoscopic surgical system 100 will be described. The endoscope 125 is a rigid-type endoscope.

As seen from FIG. 9, the endoscope 125 of the fifth embodiment comprises an elongated insertion section 126 and eyepiece portion (hand-side section) 127 located at the hand-side end of the insertion section 126. The insertion section 126 has an insertion axis Oi. The insertion section 126 includes an objective lens 128 and relay lens 129 for transmitting an image, from the affected area 103, sent from the objective lens 128. An eyepiece 130 is provided in the eyepiece portion 127.

An optical adaptor 132 having an imaging lens 131 is formed integral with the eyepiece portion 127. A TV camera 134 with a CCD 133 is formed integral with the upper end of the optical adaptor 132. The imaging lens 131 of the optical adaptor 132 can be moved along the observation optical axis Oo by a first motor 135. By moving the imaging lens 131, the focal point of the endoscope 125 at the affected area 103 side can be changed. Further, the TV camera 134 is connected to the TV monitor via a controller 33. The endoscope 125 also comprises an illumination optical system (not shown) and a light guide (not shown) for guiding the light emitted from a light source (not shown).

A cylindrical sheath 101 having a distal opening and proximal (hand-side) opening is inserted into an opening 102 formed in, for example, the head of a patient. The sheath 101 has an axis Of. The affected area 103 is observed by the endoscope 125 inserted in the opening 102 through the sheath 101, and is treated.

An endoscope support arm 141 is formed integral with the outer periphery of the sheath 101 and a cylinder 143. The cylinder 143 has a holding hole 142. The axis of the holding hole 142 of the cylinder 143 is identical to the axis Of of the sheath 101 (i.e., identical to the insertion axis Oi and observation optical axis Oo).

A screw hole 145 is formed in the outer peripheral wall of the cylinder 143, so that it extends perpendicular to the axis Of. When a fixing screw 146 is screwed into the screw hole 145, using a knob 147, it is pressed against the insertion section 126 of the endoscope 125 fitted in the cylinder 143, thereby fixing the endoscope 125 to the cylinder 143.

The sheath 101 is fixed to, for example, an operating table (not shown), by a holder arm 104 connected to the endoscope support arm 141.

An outwardly projecting annular flange 105 is formed at the hand-side opening of the sheath 101. The axis of the flange 105 is identical to that of the sheath 101, Of. A rotary cylinder 110 having a distal opening and proximal opening is received in the sheath 101 so that it can rotate about the axis Of of the sheath 101.

An outwardly projecting annular flange 106 is formed at the hand-side opening of the rotary cylinder 110. The axis of the flange 106 is identical to that of the sheath 101, Of. A screw portion 107a is provided at the outer periphery of the flange 106. Further, a cylindrical fastening ring 108 having a screw portion 107b engaged with the screw portion 107a is provided at the outer periphery of the flange 106. An internally projecting annular flange 108a is formed at distal end of the cylindrical fastening ring 108. The ring 108 is fitted on the side of the flange 105 opposing the flange 106 with the flange 105 interposed therebetween parallel to the axis Of.

A first reflection mechanism is provided at the distal opening of the rotary cylinder 110 positioned close to the affected area 3, and consists of a solenoid 118 for converting electric energy into mechanical energy. The shaft 117, i.e. axis Og of the solenoid is perpendicular to the cross-sectional plane of the rotary cylinder 100 that passes through the axis Of. A first reflection mirror 115 is provided on a swing arm 116. The swing arm 116 is attached to the shaft 117. It is preferable that the first reflection mirror 115 is inclined by 45° to the axis Of. The swing arm 116 can pivot between a first position in which the first reflection mirror 115 is positioned on the axis Of, and a second position in which the mirror 115 is retracted from the axis Of, as is indicated by the arrow in FIG. 9.

A second reflection mechanism is provided opposing the first reflecting mechanism. In other words, when the swing arm 116 is positioned in the first position, the second reflection mechanism is on the extension of the axis of the swing arm 116. The second reflection mechanism includes a second motor 123 fixed to the rotary cylinder 110, and a shaft 122, parallel to 117. This shaft 122 rotates around the axis Oh. The shaft 122 has a block 121 that rotates in accordance with the rotation of the shaft 122. A second reflection mirror 119 is attached to the block 121.

A structure that connects the endoscope 125 to the sheath 101 will be described. The insertion section 126 of the endoscope 125 is inserted through the cylinder 143, and the boundary portion of the insertion section 126 and eyepiece portion 127 is held by the cylinder 143. The screw 146 is screwed to thereby fix the endoscope 125 to the cylinder 143 in a desired position. At this time, the insertion axis Oi of the endoscope 125 is identical to the axis Of of the sheath 101.

Referring to FIG. 9, a description will now be given of the optical positional relationship between the first and second reflection mirrors 115 and 119, and the imaging lens 131 of the optical adaptor 132.

In the state indicated by the solid line in FIG. 9, the first reflection mirror 115 is positioned on the observation optical axis Oo of the endoscope 125, inclined by α with respect to the observation optical axis Oo. On the observation optical axis Oo reflected by the first reflection mirror 115, the second reflection mirror 119 is positioned inclined by β with respect to the axis Of of the sheath 101. The observation optical axis Oo reflected by the first reflection mirror 115 intersects the axis Of at point A.

The position of the imaging lens 131 of the optical adaptor 132 is controlled such that the intersection A is identical to the focal point of the endoscope 125. This position control is executed by a control mechanism 153 of the electric system described below.

As seen from FIG. 9, the first motor 135 is connected to a first driving circuit 155 that is connected to the control mechanism 153. The control mechanism 153 is connected to a second driving circuit 154 that is connected to the above-mentioned second motor 123.

The endoscopic surgical system 100 of this embodiment is provided with an operation board 150. The board 150 has a seesaw-type ON/OFF switch 151 of two levels, and a dial switch 152 having a variable resistance and enabling stepless output. The dial switch 152 is connected to the control mechanism 153. The control mechanism 153 has a logic circuit (not shown) for controlling the driving circuits 154 and 155 according to the position of the dial switch 152.

The ON/OFF switch 151 is connected to the solenoid 118 via a third driving circuit 158.

The operation of the fifth embodiment will be described. Firstly, the preparation executed before the endoscope 125 and sheath 101 are inserted into an opening 102 formed in the body of a patient will be described.

The endoscope 125 is inserted into the hole 142 of the holding cylinder 143. A surgeon then checks the image of the affected area 103 displayed on the TV monitor 34. To facilitate the operation of a surgical instrument (not shown), the endoscope 125, optical adapter 132 and TV camera 34 are rotated to adjust the orientation of the observation image on the TV monitor 34 to that of the affected area actually seen. Then, the knob 147 is turned to fasten the fixing screw 146, thereby pressing the insertion section 126 of the endoscope 125 to hold it in the cylinder 143.

A description will now be given of how the affected area 103 is observed. An image of the affected area 103 is transmitted to the optical adaptor 132 via the objective lens 128, relay lens 129 and eyepiece 130 of the endoscope 125. The image is further transmitted from the imaging lens 131 of the optical adaptor 132 to the CCD 133 of the TV camera 134. As a result, the image of the affected area 3 is displayed on the TV monitor 34 via the controller 33.

The fifth embodiment enables: ① frontal observation using the endoscope; ② change, using the mirrors, of the direction of observation, with the center of the field of view fixed; and ③ change of the angle of the observation direction ② (change of the angle of the observation optical axis Oo). ①, ② and ③ will be described in detail.

Re: ① Frontal observation using the endoscope:

When the ON/OFF switch 151 of the operation board 150 is pushed in one direction (e.g. turned off), a signal is transmitted to the solenoid 118 via the third driving circuit 158, thereby pivoting the solenoid 118 in the direction indicated by arrow 161. More specifically, the shaft 117 is rotated and the swing arm 116 attached to the shaft 117 is swung. As a result, the first reflection mirror 115 is retracted to the position indicated by the broken line in FIG. 9. In this state, the observation optical axis Oo of the endoscope 125 is directly in line with the affected area 103. Subsequently, the dial 152 is operated to drive the first motor 135 via the first driving circuit 155, thereby adjusting the focal point of the endoscope 125.

When the ON/OFF switch 151 is pushed in the other direction (e.g. turned on), the first reflection mirror 115 returns to the position indicated by the solid line in FIG. 9, as a result of the operation opposite to the above.

Re: ② Change, using mirrors, of direction of observation, with center of field of view fixed:

In the state shown in FIG. 9, the rotary cylinder 110 is rotated about the axis Of relative to the sheath 101. Accordingly, the first and second reflection mirrors 115 and 119 are rotated about the axis Of. As a result, the observation optical axis Oo draws a conical locus using the point A as the apex. Thus, the direction of observation of the affected area 103 is changed with the center of the field of view fixed, as in the aforementioned embodiments. At this time, since the endoscope 125 and TV camera 134 do not rotate, the observation image displayed on the TV monitor 34 does not rotate.

Re: ③ Change of angle of observation direction ② (change of angle of observation optical axis Oo):

When the dial switch 152 of the operation board 150 is rotated, a signal corresponding to the amount of rotation of the dial switch 152 is input to the control mechanism 153. The control mechanism 153 supplies the first and second driving circuits 155 and 154 with respective signals corresponding to the information obtained from the logic circuit that is incorporated in the mechanism. The first and second driving circuits 155 and 154 output driving signals to the first and second motors 135 and 123 to rotate them, respectively.

When the second motor 123 rotates, the shaft 122 and block 121 rotate simultaneously. As a result, the angle β of the second reflection mirror 119 formed integral with the block 121 changes. Accordingly, the angle ω between the observation optical axis Oo and the axis Of of the sheath 101 changes. On the other hand, when the first motor 135 rotates, the imaging lens 131 is moved. As a result, the focal point of the endoscope 125 is moved on the observation optical axis Oo. Thus, the focal point of the endoscope 125 is adjusted.

The control mechanism 153 may have an auto-focusing function. Also in this case, when the angle of the observation optical axis Oo to the axis Of of the sheath 101 varies, the control mechanism 153 controls the driving signals supplied to the driving circuits 155 and 154. As a result, the focal point on the observation optical axis Oo is always positioned on the axis Of. If, for example, the angle ω becomes large, the first motor 135 is rotated to move the imaging lens 131 so that the focal point of the endoscope 125 will be positioned closer to the lens 131.

By virtue of the above operations, the angle ω for observing the affected area 103 can be optionally changed as shown in FIG. 10.

Although the fifth embodiment uses optical reflection, the observation image is not reversed since reflection occurs twice. Therefore, in the fifth embodiment, it is not necessary to incorporate an image reversing circuit in the control unit 33 as in the third or fourth embodiment. Accordingly, the fifth embodiment can be made simple in structure.

To change the direction of observation with the center of the field of view fixed, it is sufficient if the first and second reflection mirrors 115 and 119 are rotated. In other words, it is sufficient if the rotary cylinder 110 is rotated relative to the sheath 101. Accordingly, the endoscope 125 does not move about within the sheath 101, which means that the endoscope 125 does not easily interrupt the operation of, for example, a surgical instrument (not shown).

The angle of the observation optical axis Oo for observing the affected area 103 can be changed by changing the angles of the first and second reflection mirrors 115 and 119. Accordingly, the affected area 103 can be observed from any desired angle. In synchronism with the change of the observation angle, the focal point of the endoscope 125 can be changed. Thus, the affected area 103 can be kept in focus even when the observation angle is changed, and hence a good observation image can be always obtained. Moreover, the auto-focusing function enables this focusing operation to be executed automatically, with the result that no complicated operation is required during a surgical operation.

Furthermore, the first reflection mirror 115 is retractable. Accordingly, observation from the front side can be performed by retracting the first reflection mirror 115 and using the endoscope as a direct-vision endoscope. Therefore, the endoscope can be used in various kinds of operations.

Figure 11:
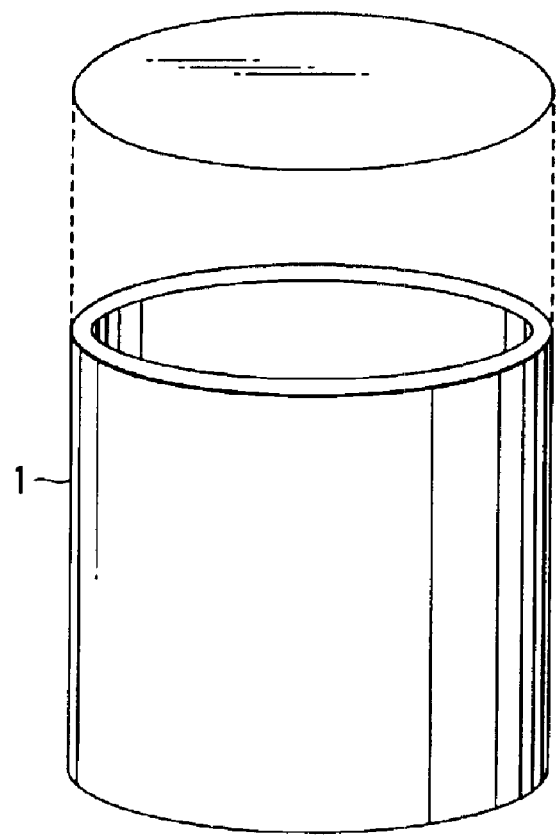
FIG. 11 is a perspective view illustrating a modification of the sheath of the endoscopic surgical apparatus.

In each of the above-described embodiments, it is preferable that the hollow sheath to be inserted into the body of a patient is a cylinder member having a completely circular cross section. However, it may have an elliptic cross section as shown in FIG. 11, or a square, rectangular or parallelogram cross section, or a polygonal cross section. The axis of the sheath usually passes through the center of a circular cross section if the sheath is cylindrical, the intersection of the major and minor axes if it has an elliptic cross section, and the intersection of the diagonal lines if it has a rectangular cross section. In other words, it is sufficient if the axis of the sheath passes through substantially the center of the sheath.

Figure 12:
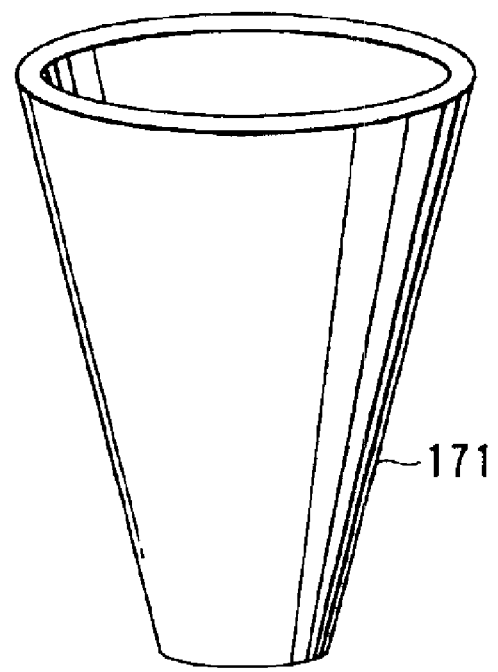
FIG. 12 is a perspective view illustrating another modification of the sheath of the endoscopic surgical apparatus.
Figure 13:
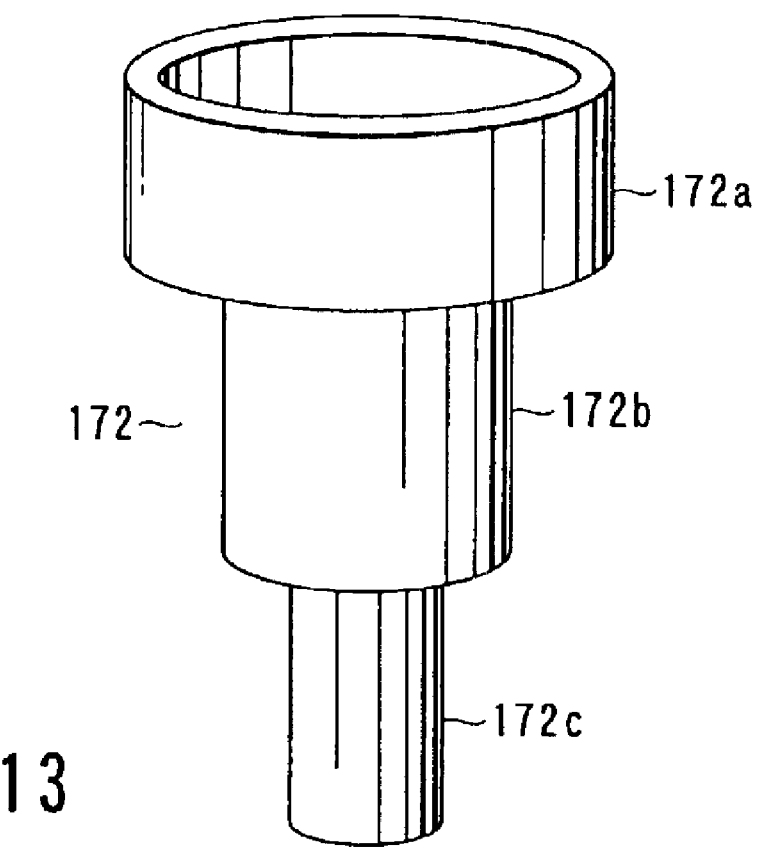
FIG. 13 is a perspective view illustrating yet another modification of the sheath of the endoscopic surgical apparatus.

Although in each embodiment, the sheath has opposite openings of the same forms and areas, they may have different forms and areas. For example, the sheath 171 shown in FIG. 12 is of a conical shape that has a wide proximal opening and narrow distal opening. The sheath 172 shown in FIG. 13 is formed of three cylindrical portions 172a, 172b and 172c arranged coaxially and having diameters gradually reduced in this order. The cylindrical portions 172a, 172b and 172c may be connected to each other such that their axes are not arranged in line.

In addition, the observation mechanism is not limited to the endoscope, but may be, for example, a microscope. Further, a pointer or reticle may be provided on the field of view of the endoscope or microscope for pointing the center of the field of view (observation optical axis). In this case, a known imaging mechanism, which includes a CCD or monitor for picking up the field of view of the endoscope or microscope, is provided to display the pointer or reticle. This structure enables reliable observation of a rotating object to be executed with the object kept at the center of the field of view.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surgical apparatus comprising:
   a rigid sheath having a distal end having a distal opening, a proximal end having a proximal opening, and an axis;
   an endoscope including an elongated, rigid insertion section having a proximal end and an insertion axis, a hand-side section connected to the proximal end of the insertion section, and an observation optical system having an observation optical axis deviated from the insertion axis of the insertion section, the endoscope being inserted into the sheath through the proximal opening; and
   a holder movably provided on the proximal end of the sheath and holding the endoscope at a position eccentric with respect to the axis of the sheath, the holder being arranged such that the observation optical axis of the endoscope intersects the axis of the sheath.

2. A surgical apparatus according to claim 1, wherein the sheath has a position limiting member provided on an outer peripheral portion of the sheath, the position limiting member holding the sheath and limiting a position of the sheath with respect to an object to be treated.

3. A surgical apparatus according to claim 2, further comprising a treatment instrument to be inserted into the sheath from the proximal opening for treating an affected area included in the object.

4. A surgical apparatus according to claim 1, wherein the holder has a rotary member, an arm projecting from the rotary member to an inside of the sheath, and an endoscope holding portion provided at an inner end of the arm, the rotary member being slidably provided on the proximal end of the sheath and rotatable about the axis of the sheath.

5. A surgical apparatus according to claim 4, wherein the sheath has a flange outwardly projecting from the proximal end, and the rotary member has a sliding portion slidable on the flange, and a cover portion covering the flange together with the sliding portion.

6. A surgical apparatus according to claim 5, wherein the cover portion has a drop prevention member for preventing the rotary member from dropping from the sheath, the drop prevention member having an outer peripheral portion immovable with respect to an inner peripheral portion of the cover portion.

7. A surgical apparatus according to claim 4, wherein the rotary member has a movement-limiting member for permitting the rotary member to rotate relative to the sheath, and inhibiting the rotary member to rotate relative to the sheath.

8. A surgical apparatus according to claim 7, wherein the movement-limiting member has a pin inserted through the rotary member toward the axis of the sheath to thereby engage the rotary member with the sheath.

9. A surgical apparatus according to claim 4, wherein:
   the endoscope holding portion has a cylindrical portion extending in a direction parallel to the axis of the sheath, an upper end of the endoscope holding portion being in contact with the end of the hand-side section; and
   the endoscope also includes a connection portion held by the endoscope holding portion between a proximal end of the insertion section and the hand-side section, the connection portion having a cross section that is perpendicular to the insertion axis and is smaller than a cross section of the hand-side section.

10. A surgical apparatus according to claim 9, wherein:
    the connection portion has a recess extending toward the insertion axis; and
    the endoscope holding portion has an endoscope engagement portion detachably received in the recess.

11. A surgical apparatus according to claim 10, wherein the endoscope engagement portion includes a pin radially extending through the endoscope holding portion and pressed toward the insertion axis.

12. A surgical apparatus according to claim 11, wherein the recess has a slit for guiding the pin, and a deep recess deeper than the slit for receiving the pin.

13. A surgical apparatus according to claim 4, wherein the holder has an arm length adjustment mechanism interposed between the arm and the endoscope holding portion, the arm length adjustment mechanism permitting the arm to be moved in directions close to and away from the endoscope holding portion.

14. A surgical apparatus according to claim 13, wherein the arm length adjustment mechanism includes a guide portion formed in the endoscope holding portion and holding the inner end of the arm.

15. A surgical apparatus according to claim 14, wherein the guide portion has a through hole and a screw received in the through hole, the screw being engaged with the inner end of the arm.

16. A surgical apparatus according to claim 2, wherein the insertion section, the hand-side section and the observation optical axis are arranged coaxial with each other, and the hand-side section includes a camera portion rotatable about the insertion axis relative to the hand-side section, the camera portion being used to pick up an image on the observation optical axis, and the camera portion having a controller with an image processing function.

17. A surgical apparatus comprising:
a rigid sheath having a distal end having a distal opening, a proximal end having a proximal opening, and an axis;
an endoscope including an elongated, rigid insertion section having a proximal end and an insertion axis, a hand-side section connected to a proximal end of the insertion section, and an observation optical system having an observation optical axis deviated from the insertion axis of the insertion section, the endoscope being inserted into the sheath through the proximal opening;
a holder holding the endoscope on the axis of the sheath and being rotatable about the axis of the sheath relative to the sheath; and
an observation optical axis deviating mechanism provided on the observation optical axis of the endoscope, the observation optical axis deviating mechanism being arranged such that the observation optical axis of the endoscope at least intersects the axis of the sheath.

18. A surgical apparatus according to claim 17, wherein the sheath has a position limiting member provided on an outer peripheral portion of the sheath, the position limiting member holding the sheath and limiting a position of the sheath with respect to an object to be treated.

19. A surgical apparatus according to claim 18, further comprising a treatment instrument to be inserted into the sheath from the proximal opening for treating an affected area included in the object.

20. A surgical apparatus according to claim 17, wherein the holder has an arm projecting from the sheath in a direction perpendicular to the axis of the sheath, and an endoscope holding portion provided at an inner end of the arm and holding the endoscope on the axis of the sheath.

21. A surgical apparatus according to claim 20, wherein:
the endoscope holding portion has a cylindrical portion having an axis identical to the axis of the sheath and the insertion axis, an upper end of the endoscope holding portion being in contact with the end of the hand-side section; and
the endoscope also includes a connection portion held by the endoscope holding portion between a proximal end of the insertion section and the hand-side section, the connection portion having a cross section that is perpendicular to the insertion axis and is smaller than a cross section of the hand-side section.

22. A surgical apparatus according to claim 18, wherein:
the observation optical axis deviating mechanism is provided at the distal end of the sheath; and
the insertion section of the endoscope has a distal end inclined to the insertion axis such that the observation optical axis is guided to the observation optical axis deviating mechanism.

23. A surgical apparatus according to claim 22, wherein the observation optical axis deviating mechanism includes a reflection mirror in the form of a circular truncated cone provided on the distal end of the sheath, the reflection mirror being tapered from the distal end toward the proximal end of the sheath, the reflection mirror making the observation optical axis intersect the axis of the sheath.

24. A surgical apparatus according to claim 22, wherein the observation optical axis deviating mechanism includes reflection mirrors provided on the distal end of the sheath, the reflection mirrors being tapered from the distal end toward the proximal end of the sheath, the reflection mirrors making the observation optical axis intersect the axis of the sheath.

25. A surgical apparatus according to claim 18, wherein the sheath has a cylindrical member provided on an inner peripheral surface thereof, the cylindrical member having a distal end and a proximal end, the cylindrical member being rotatable about the axis of the sheath relative to the sheath and having a drop prevention mechanism for preventing the cylindrical member from dropping from the sheath.

26. A surgical apparatus according to claim 25, wherein the sheath has a flange outwardly projecting from the proximal end of the sheath, and the drop prevention mechanism has a flange outwardly projecting from the proximal end of the cylindrical member, the flange of the drop prevention mechanism projecting further outwardly than the flange of the sheath, the drop prevention mechanism also having a ring member fitted on an outer periphery of the flange of the cylindrical member, the ring member cooperating with the flange of the cylindrical member in holding the flange of the sheath.

27. A surgical apparatus according to claim 25, wherein the observation optical axis deviating mechanism is provided at the distal end of the cylindrical member.

28. A surgical apparatus according to claim 27, wherein the observation optical axis deviating mechanism includes a first reflection mirror positioned on the observation optical axis of the endoscope, and a second reflection mirror positioned on the observation optical axis resulting from reflection of the first reflection mirror.

29. A surgical apparatus according to claim 28, wherein the first reflection mirror has a driving mechanism for moving the first reflection mirror between a first position in which the first reflection mirror is positioned on the observation optical axis, and a second position in which the first reflection mirror is retracted from the observation optical axis.

30. A surgical apparatus according to claim 29, wherein the observation optical axis of the endoscope is identical to the axis of the sheath.

31. A surgical apparatus according to claim 29, wherein the driving mechanism has a driving portion, a shaft and a swing arm, the driving portion being provided at the distal end of the cylindrical member, the shaft being perpendicular to the insertion axis of the endoscope and rotated by the driving portion, and the swing arm having a proximal end thereof connected to the shaft and a distal end thereof provided with the first reflection mirror.

32. A surgical apparatus according to claim 28, wherein the second reflection mirror has a rotation mechanism for making the observation optical axis, resulting from reflection of the first reflection mirror, intersect the axis of the sheath.

33. A surgical apparatus according to claim 32, wherein the rotation mechanism includes a driving portion, a shaft and a block, the driving portion opposing the first reflection mirror on the observation optical axis with the axis of the sheath interposed therebetween, the shaft being located perpendicular to the first reflection mirror positioned on the observation optical axis, the shaft being rotated by the driving portion, the block having the second reflection mirror and being rotatable together with the shaft.

34. A surgical apparatus according to claim 29, wherein the endoscope includes a focal distance varying mechanism for adjusting, onto the axis of the sheath, a focal point of the endoscope on the observation optical axis resulting from sequential reflection of the first and second reflection mirrors, and a focal point of the endoscope on the observation optical axis resulting from retraction of the first reflection mirror from the observation optical axis.

35. A surgical apparatus according to claim 34, wherein the focal distance varying mechanism includes an optical system driving mechanism for moving the observation optical system along the insertion axis.

36. A surgical apparatus according to claim 18, wherein:
the insertion section, the hand-side section and the observation optical system are coaxial; and
an upper end of the hand-side section is provided with a camera portion for picking up an image on the observation optical axis, the camera portion having a sheath integration mechanism that rotates in accordance with rotation of the sheath about the axis of the sheath, and the camera portion being rotatable relative to the hand-side section.

37. A surgical apparatus according to claim 36, wherein the camera portion is connected to a controller having a video signal processing function.

38. A surgical apparatus according to claim 37, wherein the controller also has an image reversing function.

39. A surgical apparatus according to claim 37, wherein the hand-side section has a prism for erecting an image obtained from the observation optical system.

40. A surgical apparatus comprising:
a rigid sheath having a distal end having a distal opening, a circular proximal end having a proximal opening, and an axis;
an object observation mechanism having an observation optical axis inclined to the axis of the sheath, the object observation mechanism being inserted into the sheath; and
an observation optical axis rotating mechanism for rotating the object observation mechanism about the axis of the sheath, wherein:
the object observation mechanism includes an endoscope, the endoscope having an elongated, rigid insertion section having a proximal end and an insertion axis, a hand-side section connected to the proximal end of the insertion section and an, observation optical system having an observation optical axis deviated from the insertion axis of the insertion section; and
the observation optical axis rotating mechanism includes a holder holding the endoscope at a position eccentric with respect to the axis of the sheath, the holder being arranged such that the insertion axis of the endoscope is parallel to the axis of the sheath and the observation optical axis of the endoscope intersects the axis of the sheath.

41. A surgical apparatus according to claim 40, wherein the holder has a rotary member, an arm projecting from the rotary member to an inside of the sheath, and an endoscope holding portion provided at an inner end of the arm, the rotary member being slidably provided on the proximal end of the sheath and rotatable about the axis of the sheath relative to the sheath.

42. A surgical apparatus comprising:
a rigid sheath having a distal end having a distal opening, a circular proximal end having a proximal opening, and an axis;
an object observation mechanism having an observation optical axis inclined to the axis of the sheath, the object observation mechanism being inserted into the sheath; and
an observation optical axis rotating mechanism for rotating the object observation mechanism about the axis of the sheath, wherein:
the object observation mechanism includes an endoscope, the endoscope having an elongated, rigid insertion section having a proximal end and an insertion axis, a hand-side section connected to the proximal end of the insertion section, and an observation optical system having an observation optical axis deviated from the insertion axis, the object observation mechanism also including an observation optical axis deviating mechanism for further deviating the deviated observation optical axis; and
the observation optical axis rotating mechanism includes a holder holding the endoscope at a position eccentric with respect to the axis of the sheath, the holder making the observation optical axis deviating mechanism deviate the observation optical axis to thereby make the observation optical axis intersect the axis of the sheath.

43. A surgical apparatus according to claim 42, wherein the observation optical axis deviating mechanism is provided at the distal end of the sheath, and the insertion section of the endoscope has a distal end inclined to the insertion axis to permit the observation optical axis deviating mechanism to deviate the observation optical axis.

44. A surgical apparatus according to claim 43, wherein the observation optical axis deviating mechanism includes a reflection mirror provided on the distal end of the sheath, the reflection mirror being tapered from the distal end toward the proximal end of the sheath, the reflection mirror making the observation optical axis intersect the axis of the sheath.

45. A surgical apparatus comprising:
a rigid sheath having a distal end having a distal opening, a circular proximal end having a proximal opening, and an axis;
an object observation mechanism having an observation optical axis inclined to the axis of the sheath, the object observation mechanism being inserted into the sheath; and
an observation optical axis rotating mechanism for rotating the object observation mechanism about the axis of the sheath, wherein:
the object observation mechanism includes an endoscope, the endoscope having an elongated, rigid insertion section having an insertion axis, a hand-side section provided on the proximal end of the insertion section, and an observation optical system, the object observation mechanism also including an observation optical axis deviating mechanism for deviating an observation optical axis of the endoscope; and
the observation optical axis rotating mechanism includes a holder holding the endoscope such that the axis of the sheath is identical to the insertion axis.

46. A surgical apparatus according to claim 45, wherein the sheath has a cylindrical member provided on an inner peripheral surface thereof, the cylindrical member being rotatable about the axis of the sheath relative to the sheath and having a drop prevention mechanism for preventing the cylindrical member from dropping from the sheath.

47. A surgical apparatus according to claim 46, wherein the sheath has a flange outwardly projecting from the proximal end of the sheath, and the drop prevention mechanism has a flange outwardly projecting from the proximal end of the cylindrical member, the flange of the drop prevention mechanism projecting further outwardly than the flange of the sheath, the drop prevention mechanism also having a ring member fitted on an outer periphery of the flange of the cylindrical member, the ring member cooperating with the flange of the cylindrical member in holding the flange of the sheath.

48. A surgical apparatus according to claim 47, wherein the observation optical axis deviating mechanism includes a first reflection mirror positioned on the observation optical axis of the endoscope, and a second reflection mirror positioned on the observation optical axis resulting from reflection of the first reflection mirror, the first and second reflection mirrors being provided on the distal end of the cylindrical member.

49. A surgical apparatus according to claim 48, wherein the first reflection mirror has a driving mechanism for moving the first reflection mirror between a first position in which the first reflection mirror is positioned on the observation optical axis, and a second position in which the first reflection mirror is retracted from the observation optical axis.

50. A surgical apparatus comprising:
a rigid sheath having a distal end having a distal opening, a proximal end having a proximal opening, and an axis;
an endoscope having a rigid insertion section having a proximal end, a hand-side section connected to the proximal end of the insertion section, and an observation optical system, the endoscope being inserted into the sheath through the proximal opening; and
optical axis deviating means for holding the endoscope and rotating the endoscope relative to the sheath about the axis of the sheath, with a focal point of the endoscope on an observation optical axis of the endoscope fixed, the optical axis deviating means moving the observation optical axis.

51. A surgical apparatus according to claim 50, wherein the optical axis deviating means includes support means supporting the insertion section of the endoscope parallel to the axis of the sheath, and optical axis direction limiting means for maintaining a position in which the observation optical axis intersects the axis of the sheath.

52. A surgical apparatus according to claim 51, wherein the optical axis direction limiting means has optical reflection means for reflecting the observation optical axis to the axis of the sheath.

53. A surgical apparatus according to claim 52, wherein the optical reflection means has focal distance adjusting means cooperating with the endoscope to positioning, on the axis of the sheath, the focal point of the endoscope on the observation optical axis.

54. A surgical apparatus comprising:
a rigid sheath having a distal end having a distal opening, a circular proximal end having a proximal opening and an axis;
an object observation mechanism having an observation optical axis inclined to the axis of the sheath, the object observation mechanism being inserted into the sheath; and
an observation optical axis rotating mechanism for rotating the object observation mechanism about the axis of the sheath, wherein:

the object observation mechanism includes an endoscope, the endoscope having a rigid insertion section having a proximal end and an insertion axis, a hand-side section connected to the proximal end of the insertion section, and an observation optical system having an observation optical axis deviated from the insertion axis of the insertion section; and the observation optical axis rotating mechanism has a holder for holding the endoscope when the insertion section of the endoscope is inserted in the sheath, the holder including an endoscope holding portion for holding the insertion section of the endoscope such that the insertion section is rotatable, and an arm having a distal end thereof provided with the holding portion, the arm being coupled to the sheath.

55. A surgical apparatus comprising:
a rigid sheath having a distal end with a distal opening and a proximal end with a proximal opening;
an object observation mechanism having an optical system for providing a focus; and
a rotating mechanism coupled to the object observation mechanism such that at least part of the object observation mechanism is rotatable about the focus of the optical system, at least part of the object observation mechanism being inserted in the sheath when the object observation mechanism is coupled to the rotating mechanism.

56. A surgical apparatus according to claim 55, wherein the sheath has a position limiting member provided on an outer peripheral portion of the sheath, the position limiting member holding the sheath and limiting a position of the sheath with respect to an object to be treated.

57. A surgical apparatus according to claim 55, wherein:
the object observation mechanism includes an endoscope, the endoscope having a rigid insertion section having a proximal end, a distal end and an insertion axis, and a hand-side section connected to the proximal end of the insertion section, the distal end of the insertion section being provided with the optical system such that an optical axis of the optical system is deviated from the insertion axis of the insertion section; and
the rotating mechanism includes a holder for holding the endoscope when the insertion section of the endoscope is inserted in the sheath.

58. A surgical apparatus according to claim 57, wherein the sheath has an axis, and the holder holds the endoscope at a position at which the insertion section of the endoscope is eccentric with the sheath.

59. A surgical apparatus according to claim 57, wherein the sheath has an axis, and the holder holds the endoscope at a position at which the insertion section of the endoscope is concentric with the sheath.

60. A surgical apparatus according to claim 57, wherein the holder comprises:
an endoscope holding portion for holding the endoscope,
an arm having a distal end thereof provided with the holding portion; and
a slidable member slidable with respect to the proximal end opening, the arm being coupled to the slidable member such that the focus of the optical system intersects an axis of rotation of the surgical apparatus.

61. A surgical apparatus according to claim 55, wherein:
the rotating mechanism includes a holder for holding the endoscope when the insertion section of the endoscope is inserted in the sheath, the holder including an endoscope holding portion for holding the insertion section of the endoscope such that the insertion section is rotatable, and an arm having a distal end thereof provided with the holding portion, the arm being coupled to the sheath; and the object observation mechanism includes an optical axis deviating mechanism for changing the optical axis of the optical system such that the focus of the optical system intersects the insertion axis of the insertion section of the endoscope.

62. A surgical apparatus according to claim 61, wherein the optical axis deviating mechanism is provided at the distal end of the sheath; and the insertion section of the endoscope has a distal end inclined to the insertion axis to permit the optical axis deviating mechanism to deviate the optical axis of the optical system.

63. A surgical apparatus according to claim 62, wherein the distal end of the sheath is provided with a reflection mirror in the form of a circular truncated cone, the reflection mirror being located on the optical axis of the optical system of the endoscope and tapered from the distal end toward the proximal end of the sheath to make the focus of the optical system intersect the insertion axis.

64. A surgical apparatus according to claim 62, wherein the distal end of the sheath is provided with reflection mirrors arranged in the form of a circular truncated cone, the reflection mirrors being located on the optical axis of the optical system of the endoscope and tapered from the distal end toward the proximal end of the sheath to make the focus of the optical system intersect the insertion axis.

65. A surgical apparatus according to claim 55, wherein:

the object observation mechanism includes an endoscope, the endoscope having a rigid insertion section having a proximal end, a distal end and an insertion axis, and a hand-side section coupled to the proximal end of the insertion section, the optical system being provided on the distal end of the insertion section of the endoscope, the object observation mechanism further including an optical axis deviating mechanism for further deviating the deviated optical axis of the optical system; and the rotating mechanism includes a holder for holding the endoscope such that the endoscope is rotatable about the focus of the optical system having the optical axis deviated by the optical axis deviating mechanism.

66. A surgical apparatus according to claim 65, wherein the optical axis deviating mechanism includes a first reflection mirror positioned on the optical axis of the optical system, and a second reflection mirror positioned on the optical axis resulting from reflection of the first reflection mirror, the first and second reflection mirrors being provided on the distal end.

67. A surgical apparatus according to claim 66, wherein the first reflection mirror has a moving mechanism movable between a first position in which the first reflection mirror is positioned on the optical axis of the optical system of the endoscope, and a second position in which the first reflection mirror is retracted from the optical axis.

68. A surgical apparatus according to claim 67, wherein the moving mechanism has a driving portion provided on the distal end of the sheath, a shaft to be rotated by the driving portion, and a swing arm, the swing arm having a proximal end thereof coupled to the shaft and a distal end thereof provided with the first reflection mirror.

69. A surgical apparatus according to claim 66, wherein the second reflection mirror has a pivot mechanism for making the optical axis, resulting from reflection of the first reflection mirror, intersect the insertion axis.

70. A surgical apparatus according to claim 69, wherein the pivot mechanism includes a driving portion, a shaft and a block, the shaft driven by the driving portion and located on the distal end of the sheath, and the block having the second reflection mirror and being rotatable together with the shaft.

71. A surgical apparatus according to claim 67, wherein the endoscope includes a focal distance varying mechanism for adjusting, onto the insertion axis, a focus of the optical system resulting from sequential reflection of the first and second reflection mirrors, and a focus of the optical system obtained when the first reflection mirror is retracted from the optical axis.

72. A surgical apparatus according to claim 65, wherein the sheath has an axis and the holder holds the endoscope at a position at which the insertion axis of the endoscope corresponds to the axis of the sheath.

73. A surgical apparatus according to claim 72, wherein the optical axis deviating mechanism includes a first reflection mirror positioned on the optical axis of the optical system, and a second reflection mirror positioned on the optical axis resulting from reflection of the first reflection mirror, the first and second reflection mirrors being provided on the distal end.

74. A surgical apparatus according to claim 73, wherein the first reflection mirror has a moving mechanism movable between a first position in which the first reflection minor is positioned on the optical axis of the optical system of the endoscope, and a second position in which the first reflection mirror is retracted from the optical axis.

75. A surgical apparatus according to claim 74, wherein the moving mechanism has a driving portion provided on the distal end of the sheath, a shaft to be rotated by the driving portion, and a swing arm, the swing arm having a proximal end thereof coupled to the shaft and a distal end thereof provided with the first reflection mirror.

76. A surgical apparatus according to claim 73, wherein the second reflection mirror has a pivot mechanism for making the optical axis, resulting from reflection of the first reflection mirror, intersect the insertion axis.

77. A surgical apparatus according to claim 76, wherein the pivot mechanism includes a driving portion, a shaft and a block, the driving portion opposing the first reflection mirror with respect to the insertion axis, the shaft driven by the driving portion and located intersecting an extension of a line segment obtained by connecting a position of the first reflection mirror on the distal end of the sheath and the insertion axis, and the block having the second reflection mirror and being rotatable together with the shaft.

78. A surgical apparatus according to claim 74, wherein the endoscope includes a focal distance varying mechanism for adjusting, onto the insertion axis, a focus of the optical system resulting from sequential reflection of the first and second reflection mirrors, and a focus of the optical system obtained when the first reflection mirror is retracted from the optical axis.

79. A surgical apparatus according to claim 40, wherein the sheath has a position limiting member provided on an outer peripheral portion of the sheath, the position limiting member holding the sheath and limiting a position of the sheath with respect to an object to be treated.

80. A surgical apparatus according to claim 42, wherein the sheath has a position limiting member provided on an outer peripheral portion of the sheath, the position limiting member holding the sheath and limiting a position of the sheath with respect to an object to be treated.

81. A surgical apparatus according to claim 45, wherein the sheath has a position limiting member provided on an outer peripheral portion of the sheath, the position limiting member holding the sheath and limiting a position of the sheath with respect to an object to be treated.

82. A surgical apparatus according to claim 1, wherein the endoscope is held by the holder such that the endoscope can rotate about the insertion axis thereof.

83. A surgical apparatus according to claim 17, wherein the endoscope is held by the holder such that the endoscope can rotate about the insertion axis thereof.

84. A surgical apparatus according to claim 40, wherein the endoscope is held by the holder such that the endoscope can rotate about the insertion axis thereof.

85. A surgical apparatus according to claim 42, wherein the endoscope is held by the holder such that the endoscope can rotate about the insertion axis thereof.

86. A surgical apparatus according to claim 45, wherein the endoscope is held by the holder such that the endoscope can rotate about the insertion axis thereof.

87. A surgical apparatus according to claim 55, wherein the object observation mechanism is operatively coupled to the rotating mechanism, and rotatably held by the rotating mechanism.

* * * * *